United States Patent [19]

Goulay

[11] 3,974,215

[45] Aug. 10, 1976

[54] PROCESS FOR DIRECTLY OBTAINING THE CALCIUM AND MAGNESIUM SALTS OF THE N-ACETYL-AMINO-6-HEXANOIC ACID FROM ACETYL-CAPROLACTAME

[75] Inventor: Jean Goulay, Oissel, France

[73] Assignee: Choay S.A., Paris, France

[22] Filed: Mar. 13, 1974

[21] Appl. No.: 450,732

[30] Foreign Application Priority Data
Mar. 13, 1973 France .............................. 73.08871

[52] U.S. Cl. ............................................. 260/534 R
[51] Int. Cl.² ...................................... C07C 102/00
[58] Field of Search ................................. 260/534 R

[56] References Cited
UNITED STATES PATENTS

| | | | |
|---|---|---|---|
| 2,327,119 | 8/1943 | Martin | 260/534 R |
| 3,655,748 | 4/1972 | Tandara | 260/534 R |

FOREIGN PATENTS OR APPLICATIONS

| | | | |
|---|---|---|---|
| 897,991 | 4/1945 | France | 260/534 R |
| 29,487 | 9/1970 | Japan | 260/534 R |
| 790,503 | 2/1958 | United Kingdom | 260/534 R |

OTHER PUBLICATIONS

Chemical Abstracts, vol. 76, 103777g, (1972), [Abstract of French Patent, 2,062,873, 8/6/71].
Chemical Abstracts, vol., 4141f, (1959).
Beilsteins, Handuch der Organischen Chemie, Vierte Auflage, Drittes Erganzungswerk, Vierterband, p. 1396 (1963).

Primary Examiner—Richard L. Raymond
Attorney, Agent, or Firm—Weiser, Stapler & Spivak

[57] ABSTRACT

A process for preparing the calcium or magnesium salt of N-acetyl-amino-6-hexanoic acid which comprises reacting directly acetyl-caprolactame with calcium or magnesium hydroxide within an aqueous solution.

18 Claims, No Drawings

PROCESS FOR DIRECTLY OBTAINING THE CALCIUM AND MAGNESIUM SALTS OF THE N-ACETYL-AMINO-6-HEXANOIC ACID FROM ACETYL-CAPROLACTAME

The invention relates to a new process for obtaining calcium and magnesium salts of N-acetyl-amino-6-hexanoic acid, also referred to as $\epsilon$-amino-caprotic acid or acexamic acid.

One of the processes used until now for producing the calcium or magnesium salts of acexamic acid from acetyl-caprolactame comprises two steps, i.e. the hydrolysis of acetyl-caprolactame for producing acexamic acid and then the reaction of the acexamic acid obtained with the hydroxide or oxide of calcium or magnesium, depending upon whether the calcium acexamate or the magnesium acexamate is desired. These two steps may be illustrated by the following reactions:

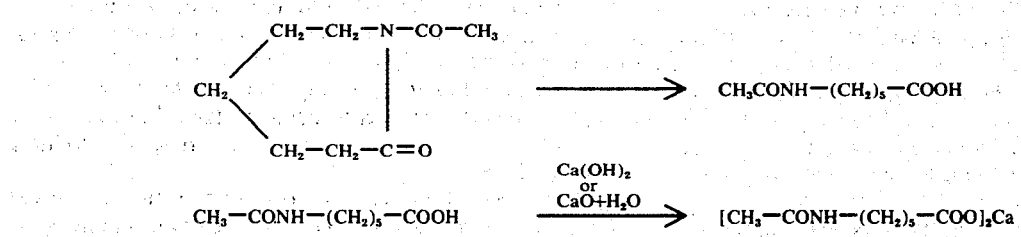

The first step is difficult to perform and enables only a low yield, because side-reaction of hydrolysis which produces a deacetylation of the acetyl-caprolactane heavily interferes with the desired reaction of hydrolysis, i.e. that which causes the caprolactame cycle to be opened to produce the acexamic acid. The caprolactame produced may of course be retransformed into acetyl-caprolactame by an acetylating reaction. In any case however this process, besides its low yield, involves the use of heavy equipment and important labor, is time consuming, and also requires repeated controls with respect to the quality of the intermediate products.

The second step is also difficult to carry out, because the crystallisation operation of the calcium or magnesium acexamate, as the case may be, is difficult. Two successive crystallisation operations at least, and sometimes more, particularly as disclosed in French Pat. No. 6,932,798 of Sept. 25, 1969, are required in order to obtain a reasonable yield.

The object of the invention is to overcome the different drawbacks discussed hereabove; more particularly the object of the invention is to provide a process for obtaining the magnesium or calcium salt of acexamic acid in a highly purified crystallin state, which can be carried out more rapidly, with reduced equipment and labor.

The process according to the invention comprises reacting directly the acetyl-caprolactame with the calcium or magnesium hydroxide as the case may be within an aqueous solution.

Advantageously the reaction is performed in the presence of an amount of water sufficient to dissolve the whole amount of calcium or magnesium salt formed, the latter salt being then recovered, such as by concentration of the solution and crystallisation. Advantageously the solution is filtered before being concentrated, in order to remove the calcium or magnesium carbonate formed in the medium as a result of the carbonation of the calcium or magnesium hydroxide used in the reaction.

In the production of calcium acexamate the pH of the medium is preferably maintained between about 7.5 and about 7.8, and in the production of magnesium acexamate, preferably between about 6.5 and about 7.

The salt obtained may contain substantial amounts of unreacted acetyl-caprolactame when the process is operated at a pH lower than the corresponding one of the lower limit values indicated hereabove. At a pH above the corresponding one of the above-indicated upper limit values, the salt obtained contains proportions of calcium acetate or magnesium acetate, as the case may be, which may become substantial. This acetate which is then precipitated together with the calcium or magnesium acexamate, is the result of the partial deacetylation of amounts of acetyl-caprolactame which has not been prevented.

When the reaction is performed at pH values between the above-indicated pH limit, a calcium or magnesium acexamate is obtained which exhibits a very high state of purity, above 99%. Such purities are greater than the best values (97%) which can be obtained by the above-indicated known process, under particularly well selected conditions of operation.

The possibility that calcium or magnesium acexamate could be produced in a crystallised form by direct hydrolysis of acetyl-caprolactame in presence of calcium or magnesium hydroxide was all the more unexpected that the corresponding reaction cannot be carried out with the corresponding sodium salt and that similar attempts for producing the crystallised calcium or magnesium salt of the N-propionly-amino-6-hexanoic acid from propionyl-caprolactame under similar operating conditions were fully unsuccessful.

The high yields ranging from about 45 to about 50%, which are obtained by the hydrolysis of acetyl-caprolactame in presence of calcium or magnesium hydroxide and by a single crystallisation are also remarkable.

Other features of the invetnion will become apparent in the course of the following description of examples of production of the magnesium or calcium acexamate.

EXAMPLE 1

Description of a preferred production procedure of the calcium or magnesium acexamate by hydrolysis of the corresponding acetyl-caprolacetame in the presence of calcium or magnesium hydroxide This preferred procedure is described hereafter as applied to the calcium salt.

The reaction is carried out in a reactor so arranged as to permit control of the temperature of the reaction medium; advantageously recourse is had to a double walled stainless steel reactor in which steam, hot or cold water or brine, etc. can be circulated. The acetyl-caprolactame and water, preferably demineralized water, are introduced simultaneously into the reactor, under stirring, the temperature of the mixture being adjusted between about 20°C and about 60°C, preferably at 25°C. The calcium hydroxide is added stepwise and under amounts which permit easy control of the temperature at a value between about 20°C and about 50°C, preferably between about 25°C and about 30°C, by resorting to an external cooling, for instance by circulating cold water at 2°C between the walls of the double walled reactor.

The duration of the introduction of the calcium hydroxide generally ranges from about 1 to about 3 hours. Stirring is maintained during the time necessary for obtaining a complete reaction, for instance during 14 hours, at a temperature ranging from about 20°C to about 50°C, preferably of about 30°C.

The pH of the medium is maintained at a value between 7.5 and 7.8 during the whole duration of the reaction. It will be appreciated that the calcium carbonate often contained in the used limes (carbonated limes) may cause the pH to move out from the above-indicated range; it must then be brought back into the desired range by adding either acetyl-caprolactame or calcium hydroxide, depending upon whether it becomes too high or too low.

After filtration of the hydrolysate, particularly for removing the small amounts of insoluble calcium carbonate contained in the medium, the clear solution is concentrated at low temperature, particularly between 40°C and 60°C, under reduced pressure, up to about half of its initial volume. Crystallisation starts as soon as the concentration operation is stopped. However, the medium is left standing for a time sufficient for enabling complete crystallisation, for instance during 24 hours.

The crystals of calcium acexamate are then washed, for instance with acetone, for removing the residual mother liquors. They are then dried under vacuum, preferably at a temperature ranging from about 40°C to about 60°C, whereby crystals of pure calcium acexamate are obtained, which requires no further purification step.

The same procedure is applicable to the production of magnesium acexamate, except for the pH of the reaction medium, which is adjusted at a value between 6.5 and 7 and, if need be, maintained at such value by adding either acetylcaprolactame or magnesium hydroxide.

EXAMPLE 2

Detailed description of the production of calcium acexamate [$CH_3-CO-NH-(CH_2)_5-COO]_2CA,H_2O$ 400 liters of demineralized water, 5 kg of calcium hydroxide, and 155 kg (1000 moles) of acetyl-caprolactame are introduced under stirring and at a temperature of about 25°C into a 1000 liters stainless double walled reactor.

The temperature is raised to 30°C. 75 kg of calcium hydroxide are introduced stepwise in the form of successive amounts of 2 kg each in the medium, under stirring and at a temperature adjusted and maintained between 25°C and 30°C through external cooling, in a manner such that the time required to introduce into the reactor the whole amount of calcium hydroxide approximates one hour and a half. When the stirring is stopped, the pH is checked, it being understood that it should lie between about 7.5 and 7.8.

The obtained mixture is stirred continuously at a temperature of 30°C during 14 hours. At the end of this operation the pH is checked again and, if need be, adjusted at a value between 7.5 and 7.8.

The hydrolysate is filtered on a 60×60 pressfilter comprising 6 compartments and equipped with fabrics of the polyester known under the designation TERGAL which have been previously coated with a suspension of a cellulose commercialized under the trademark SOLKA FLOX BW20. The duration of filtration is of one hour and a half. 580 liters of the filtrate are recovered and subjected to a concentration under reduced pressure in an evaporator the volume of which is of 750 liters, at a distillation temperature ranging from 45°C to 50°C, under a reduced pressure of 10 to about 15 Torr.

The operation is ran until concentration of the solution to 280 liters, the concentrated solution being then left standing. The crystallisation is already considerable two hours after the end of the operation of concentration. Crystallisation is ended after 16 to 24 hours.

The crystals are centrifuged at a speed of 700 revolutions/minute. The centrifuged crystals of calcium acexamate are washed twice on the centrifuge with 20 liters of acetone.

107 kg of crystals are obtained, which are dried under vacuum at 40°C. The 96 kg of dry calcium acexamate obtained are ground and sifted. Analysis yielded the following results:

| | |
|---|---|
| Yield | : 45% |
| Aspect | : White powder |
| Losses after a dessication operation | : Lower than 1% |

A 5% solution of that calcium acexamate is clear.

| | |
|---|---|
| Contents in calcium | : 9.95% |
| Titre in calcium acexamate | : Higher than 99% |
| Contents in crystallisation water | : 4.5% |

EXAMPLE 3

Preparation of magnesium acexamate 400 liters of demineralized water, 5 kg of magnesium hydroxide and 105 kg (1000 moles) of acetyl-caprolactame are introduced in the same double walled reactor under stirring at 25°C.

The temperature is adjusted between 25°C and 30°C; 28 kg of magnesium hydroxide are added stepwise in the form of successive amounts of 1 kg, such that the duration of introduction of the total amount of magnesium hydroxide is of about 1 hour.

When the introduction of magnesium hydroxide has been completed, the temperature is increased up to 60°C by external heating, said temperature being then maintained for about 15 minutes, whereby the time necessary for hydrolysis is reduced. The medium is then cooled at 30°C and the pH checked so that it be comprised between 6.5 and 7.

The solution is filtered under the same conditions as in Example 2, over a period of 2 hours.

The 580 liters of filtrate which are collected are concentrated under vacuum in an evaporator the volume of which is 750 liters, at a distillation temperature of 45°C—50°C, under a reduced pressure of 10 to 15 Torr, until a 290 liters volume of concentrated solution is obtained.

The concentrated solution is then left standing and crystallisation of magnesium acexamate is induced by adding therein 200 g of crystals obtained during a preceding crystallisation operation. The crystallisation is ended after 16 hours.

The crystals are centrifuged under the same conditions than in Example 2, then washed twice, each time with 20 liters of acetone.

The total weight of crystals obtained is 110 kg. The total weight of crystals obtained after drying under vacuum at 40°C, grinding and sifting, is of 101 kg.

The analysis yields the following results:

| | |
|---|---|
| Yield | : 51% |
| Aspect | : White powder |
| Losses after dessication | : Lower than 1% |
| Aspect of a 5% solution of magnesium acexamate | : Clear |
| Contents in magnesium | : 7.6% |
| Titre of magnesium acexamate | : 99.2% |

The process according to the invention for preparing calcium acexamate or magnesium acexamate can thus be carried out in an easy and rapid manner, and is able to produce pure products after a single crystallisation operation. This process thus enables an important reduction of the production cost of the calcium and magnesium salts of acexamic acid, which salts are, as is well known, valuable active principles for drugs.

What we claim is:

1. Process for preparing the calcium or magnesium salt of N-acetyl-amino-6-hexanoic acid which comprises reacting directly acetyl-caprolactam with calcium or magnesium hydroxide within an aqueous solution at a reactive temperature, and collecting a solution of the salt product.

2. Process according to claim 1 for the production of calcium acexamate, wherein the pH of the reaction medium is adjusted and maintained at a value between about 7.5 and about 7.8.

3. Process according to claim 1 for the production of magnesium acexamate, wherein the pH of the medium is adjusted and maintained at a value between about 6.5 and about 7.

4. Process according to claim 1 wherein the reaction is carried out in presence of an amount of water sufficient for dissolving all of the calcium or magnesium salt of N-acetyl-amino-6-hexanoic acid formed during the reaction, and wherein the solution obtained is then concentrated and the salt of calcium or magnesium is then crystallised in the solution.

5. The process of claim 1 which comprises removing.

6. The process of claim 1 which comprises further concentrating the solution of the salt product.

7. The process of claim 6 which comprises further concentrating the concentrate and recovering crystals of the salt formed.

8. The process of claim 1 which comprises the further step of adjusting the pH to a reactive pH.

9. The process of claim 8 wherein the reactive pH is in the range of about 6.5 to about 7.8.

10. The process for preparing crystalline calcium or magnesium salt of N-acetyl-amino-6-hexanoic acid which comprises bringing together and reacting directly acetyl-caprolactam with calcium or magnesium hydroxide, respectively, in an aqueous medium and separating the formed crystalline calcium or magnesium salt of N-acetyl-amino-6-hexanoic acid by crystallization.

11. The process of claim 10 wherein the pH range is maintained in the range of about 6.5 to 7.8.

12. The process of claim 10 wherein the temperature is maintained at the reaction temperature for the acetylcaprolactam and the calcium or magnesium hydroxide.

13. The process of claim 12 wherein the temperature is maintained in the range of about 20° to about 50°C, for obtaining maximum yields.

14. The process of claim 13 wherein the temperature is maintained in the range of about 25° to 30°C.

15. The process of claim 10 for the production of the calcium salt of N-acetyl-amino-7-hexanoic acid in a highly purified crystalline state which comprises adjusting and maintaining the pH of the reaction medium at a value between about 7.5 and about 7.8, removing any insoluble calcium or magnesium carbonate by-product formed, recovering the clear solution, and crystallising directly the calcium salt of N-acetyl-amino-6-hexanoic acid in a highly purified crystalline state from said solution.

16. The process of claim 15 wherein said clear solution is concentrated at a temperature from about 40°C to about 60°C under reduced pressure up to about half of its initial volume and recovering said calcium salt of hexanoic acid in a highly purified crystalline state from the concentrated solution.

17. The process of claim 10 for the production of the magnesium salt of N-acetyl-amino-6-hexanoic acid in a highly purified crystalline state which comprises adjusting and maintaining the pH of the reaction medium at a value comprised between about 6.5 and about 7, removing any insoluble calcium or magnesium carbonate by-product formed, recovering the clear solution, and crystallising directly the magnesium salt of Nacetyl-amino-6-hexanoic acid in a highly purified crystalline state from said solution.

18. The process of claim 17 wherein said clear solution is concentrated at a temperature from about 40°C to about 60°C under reduced pressure up to about half of its initial volume and recovering said magnesium salt of hexanoic acid in a highly purified crystalline state from the concentrated solution.

* * * * *